United States Patent [19]

Blumberg et al.

[11] Patent Number: 5,232,684

[45] Date of Patent: Aug. 3, 1993

[54] LABELLED RESINIFERATOXIN, COMPOSITIONS THEREOF, AND METHODS FOR USING THE SAME

[75] Inventors: Peter M. Blumberg, Frederick; Arpad Szallasi, Bethesda, both of Md.; Zoltan Szallasi, Washington, D.C.

[73] Assignee: The United States of America as represented by the Department of Health and Human Services, Washington, D.C.

[21] Appl. No.: 546,141

[22] Filed: Jun. 29, 1990

[51] Int. Cl.$^5$ .................... A61K 49/02; C07D 323/00; G01N 33/567

[52] U.S. Cl. .................... 424/1.1; 549/348; 424/7.1; 436/503; 436/504

[58] Field of Search .................... 424/1.1, 7.1; 549/348; 436/503, 504, 800, 804

[56] References Cited

U.S. PATENT DOCUMENTS 4,939,149 7/1990 Blumberg ............................ 514/691
5,021,450 6/1991 Blumberg ............................ 514/453

OTHER PUBLICATIONS

*Isotopes in the Physical and Biomedical Sciences, vol. 1 Labelled Compounds (Part A),* Chapter 6 by Filer.
*The Pharmacologist,* Aug. 1989.
"RadioTracer Techniques and Applications", vol. 1, edited by Evans et al., Chaper 5.
Szallasi, et al., *Neuroscience,* 30 (1989) 515–520.
James, et al., *Molecular Pharmacology,* 33:643–649.
deVries, et al., *Life Sciences,* 44: 711–715, 1989.
*Journal of Natural Products,* May–Jun., 1982, vol. 45, No. 3 by Adolf et al.
Synthesis and Applications of Isotopically Labelled Compounds, pp. 273–274, 1988, by Harris et al.
Synthesis and Applications of Isotopically Labelled Compounds, pp. 267–271, by Silver.
Dictionary of Biochemistry & Molecular Biology, 2d Ed.; 1989.
Chem Abs., vol. 84, No. 21, abs 145695z (1975) Schmidt et al., *J. Pharm. Pharmacol.,* 27 Suppl.

*Primary Examiner*—Robert L. Stoll
*Assistant Examiner*—John M. Covert
*Attorney, Agent, or Firm*—Birch, Stewart, Kolasch & Birch

[57] ABSTRACT

The present invention relates to labelled resiniferatoxin and congeners thereof. Preferably, the labelled compounds of the invention are radio or fluorescently labelled. The invention is further directed to compositions comprising these labelled compounds, as well as to methods of using these compounds.

30 Claims, 2 Drawing Sheets

LABELLED RESINIFERATOXIN, COMPOSITIONS THEREOF, AND METHODS FOR USING THE SAME

BACKGROUND OF THE INVENTION

1. Field of the Invention

The present invention relates to labelled resiniferatoxin or labelled congeners thereof, compositions thereof, and methods of using these labelled compounds.

2. Description of Related Art

Capsaicin activates a specific class of neurons (sensory C-fiber afferent neurons) which contain tachykinins (e.g., substance P and calcitonin gene related peptide) and are involved in the perception of pain, thermoregulation, and neurogenic inflammation (Buck, S.H. and Burks, T.F., The neuropharmacology of capsaicin: review of some recent observations, Pharmacol. Rev., 38 (1986) 179-226; Holzer, P., Local effector functions of capsaicin-sensitive sensory nerve endings: involvement of tachykinins, calcitonin gene-related peptide and other neuropeptides, Neuroscience, 24 (1988) 739-768.) The initial activation of the neurons is followed by long-lasting desensitization (Jancso, N., Jancso-Gabor, A. and Szolcsanyi, J., Direct evidence for neurogenic inflammation and its prevention by denervation and by pretreatment with capsaicin, Br.J.Pharmacol.-Chemother., 31 (1969) 138-151; Monsereenosurn, Y., Kongsamut, S. and Pezalla, P.D., Capsaicin- a literature survey, CRC Crit Rev.Toxicol., 10 (1982) 321-339) and capsaicin analogs have therefore been of interest as potential non-narcotic analgesics. (Maggi, C.A. and Meli, A., The sensory-efferent function of capsaicin-sensitive sensory neurons, Gen.Pharmac., 19 (1988) 1-43). The biochemical mechanism of capsaicin action remains unknown. It appears, however, that a rapid response is increased membrane conductance of cations, including $Ca^{++}$, $Na^+$, and $K^{+16}$; inhibition of $Ca^{++}$ influx either through use of $Ca^{++}$free medium (Santiciolini, P., Patacchini, R., Maggi, C.A. and Meli, A., Exposure to calcium-free medium protects sensory fibers by capsaicin desensitization, Neurosci. Lett., 80 (1987) 167-172) or by treatment with ruthenium red (Maggi, C.A., Patacchini, R., Santicoli, P., Giuliani, S., Geppetti, P. and Meli, A., Protective action of Ruthenium red toward capsaicin desensitization of sensory fibers, Neurosci. Lett., 88 (1988) 201-205) blocks the desensitization. The identification of the putative capsaicin receptors has been precluded by the lipophilicity of capsaicin and by its relatively low potency.

Recently, resiniferatoxin (RTX), a diterpene combining structural features of the phorbol ester tumor promoters and of capsaicin, has been demonstrated to function as an ultrapotent capsaicin analog (deVries, D.J. and Blumberg, P.M., Thermoregulatory effects of resiniferatoxin in the mouse: comparison with capsaicin, Life Sci., 44 (1989) 711-715; Szallasi, A. and Blumberg, P.M., Resiniferatoxin, a phorbol-related diterpene, acts as an ultrapotent analog of capsaicin, the irritant constituent in red pepper, Neuroscience, 30 (1989) 515-520). RTX induces pain, hypothermia, and neurogenic inflammation; the acute responses are followed by desensitization to RTX and by cross-desensitization to capsaicin (deVries, D.J. and Blumberg, P.M., Thermoregulatory effects of resiniferatoxin in the mouse: comparison with capsaicin, Life Sci., 44 (1989) 711-715; Szallasi, A. and Blumberg, P.M., Resiniferatoxin, a phorbol-related diterpene, acts as an ultrapotent analog of capsaicin, the irritant constituent in red pepper, Neuroscience, 30 (1989) 515-520). RTX differs from capsaicin, however, both in its potency and selectivity. RTX is $10^3$-$10^4$ fold more potent for hypothermia and neurogenic inflammation but only comparable in potency for induction of pain (Szallasi, A. and Blumberg, P.M., Resiniferatoxin, a phorbol-related diterpene, acts as an ultrapotent analog of capsaicin, the irritant constituent in red pepper, Neuroscience, 30 (1989) 515-520). Our in vivo findings have been recently confirmed by in vitro experiments: RTX showed potent capsaicin-like actions both on cultured sensory neurons and in the isolated spinal cord-/tail preparation (Winter, J., Dray, A., Wood, J.N. and Bevan, S.J., Resiniferatoxin is a potent capsaicin-like sensory neurotoxin, Soc. Neurosci. Abstr., 18 (1989) 176.8).

*Isotopes in the Physical and Biomedical Sciences, Vol. 1, Labelled Compounds (Part A)*, Chapter 6, by Filer discloses the preparation and characterization of tritiated neurochemicals. Section 2, subsection 2.3 of Chapter 6 discloses catalytic dehalogenations with tritium.

"RadioTracer Techniques and Applications", Vol. 1, edited by Evans et al., Chapter 5, discloses the preparation of radiotracer compounds.

Szallasi, et al., *Neuroscience*, 30 (1989) 515-520 disclose that resiniferatoxin, a phorbol-related diterpene, acts as an ultrapotent analog of capsaicin, the irritant constituent in red pepper.

James, et al., *Molecular Pharmacology*, 33: 643-649, discloses long-lasting agonist activity produced by a capsaicin-like photoaffinity probe.

deVries, et al., *Life Sciences*, 44: 711-715, 1989, discloses the thermoregulatory effects of resiniferatoxin in the mouse and a comparison with capsaicin.

*Journal of Natural Products*, May-June, 1982, Vol. 45, No. 3 by Adolf et al, discloses the structure-activity relations of polyfunctional diterpenes of the Daphnane Type, and the revised structure for resiniferatoxin and structure-activity relations of resiniferol and some of its esters.

Synthesis and Applications of Isotopically Labelled Compounds, p. 273-274, 1988, by Harris et al discloses iodine-labelled growth factors in biochemical research and receptors for platelet derived growth factor (PDGF).

Synthesis and Applications of Isotopically Labelled Compounds, pp. 267-271, by Silver discloses radioiodination techniques.

SUMMARY OF THE INVENTION

The present invention relates to labelled resiniferatoxin and congeners thereof. Preferably, the labelled compounds of the invention are radio or fluorescently labelled. The invention is further directed to compositions comprising these labelled compounds, as well as to methods of using these compounds.

BRIEF DESCRIPTION OF THE DRAWINGS

The present invention will become more fully understood from the detailed description given hereinbelow, and the accompanying drawings which are given by way of illustration only, and thus are not limitative of the present invention.

FIG. 1. Specific binding of [$^3$H]RTX to the membrane fraction from rat DRG. FIG. 1/a: binding curves for total (△), specific (○), and nonspecific (●) bound values. Each point represents the mean for 3 separate experiments done on separately prepared membrane fractions. Error bars indicate SEM. Nonspecific binding is determined in the presence of excess nonradioactive RTX (100–1000 nM). The theoretical binding curves are calculated by using the $K_d$ and $B_{max}$ values from the Scatchard analysis. FIG. 1/b: Scatchard plot of specific [$^3$H]RTX binding. The line is fitted using the LIGAND program. Points represent mean values from single experiments. Data are normalized to 1 mg membrane protein in 0.15 ml assay volume. FIG. 1/c: Inhibition of [$^3$H]RTX binding by nonradioactive RTX. Each point represents the mean for 3 experiments SEM is indicated by the error bars.

DETAILED DESCRIPTION OF THE INVENTION

Capsaicin stimulates and then desensitizes sensory afferent C-fibers and the hypothalamic temperature control region. The induced desensitization may have application in arthritis, asthma, allergic responses including rhinitis, fever, pain associated with herpetic neuralgia or cancer, and in biological processes mediated by tachykinins, including substance P. Resiniferatoxin is a naturally occurring ultrapotent capsaicin analog having the following structure:

One aspect of the present invention relates to a method for the preparation of [3H]labelled resiniferatoxin or labelled congeners thereof. The radiolabelled compound is novel although the non-radioactive compound per se is known. The invention is further directed to novel methods of using the labelled compounds of the invention, including, for instance, to demonstrate and characterize specific capsaicin receptors. Such assays will be valuable to the pharmaceutical industry to evaluate synthetic capsaicinoids, to screen for novel natural products acting on these receptors, and to assay concentrations and amounts of such compounds.

Labelled resiniferatoxin or labelled congeners thereof of the invention include radiolabelled compounds thereof, wherein representative radiolabels include tritium, I-131 and I-125.

Labelled resiniferatoxin and congeners thereof of the invention also include fluorescently labelled compounds thereof, wherein representative fluorescent labels are selected from the group consisting of fluorescein, rhodamine, eosin, erythrosin, pyrene, anthracene, acridine, dimethylaminophytyl and 7-nitrobenzo-2-oxa-1,3-diazole (NBD).

Representative congeners of RTX include those of formula II:

where $R_3$ is OH, X is 0 or 1, $R_1$, $R_2$, $R_4$ and $R_5$ each are: H, OH, $$OC(CH_2)_nH, O(CH_2)_nH$$

with n=0 to 10.

In labelled compounds of formula (II), at least one of $R_1$, $R_2$, $R_4$ or $R_5$ is labelled, for instance, with [$^3$], $^{125}$I or $^{131}$I.

A preferable congener of RTX is tinyatoxin.

A preferred labelled compound and composition containing the same has the formula:

(III)

Other representative congeners of RTX include those of formula IV:

(IV)

n is 0 to 10, preferably 2, and
wherein R' is a fluorescent label.

An alternative for detection of specific receptor binding with radiolabelled resiniferatoxin or its labelled congeners is by the use of a fluorescent analog and by detection on the basis of this fluorescence. Two classes of such analogs, although not the only classes of such fluorescent analogs, are as follows:

1. Congeners of resiniferatoxin in which the homovanillic ac

(VII)

n is 0 to 10, preferably 2, and
wherein R[1] is 7-nitrobenz-2-oxa-1,3-diazole coupled at the 4 position, or as shown below.

(VIII)

(IX)

n is 0 to 10, preferably 2, and
wherein R represents the fluorescein-5-, the fluorescein-6-, the rhodamine-5-, the rhodamine-6-, the tetramethylrhodamine-6-, the sulforhodamine-6-, the eosin-5-, the erythrosin-5-, the pyrene-1-, the antracene-2, the acridine-9-, or the 4-dimethylaminophthyl-1- group.

Other fluorescent groups used by workers skilled in the art to label compounds for detection in biological or biochemical systems may alternatively be used, and the above description should not be construed to limit the scope of the invention.

The invention is also directed to compositions comprising an effective amount of labelled RTX or congeners thereof for demonstrating, quantitating, or otherwise characterizing specific binding to its receptors via the resiniferatoxin/capsaicin/vanilloid receptors, and a suitable carrier.

The compounds of the invention, RTX and Tinyatoxin may be prepared using the methodology for esterification as set forth in J. Natural Prod., Vol. 45, p. 348 (1982), and in copending application 07/358,073, filed May 5, 1988.

RTX qualitatively resembles capsaicin in its activity, but differs quantitatively in potency (i.e., $10^3$–$10^4$ fold more potent) and in relative spectrum of actions. Resiniferatoxin, tinyatoxin (TTX) and the congeners thereof thus cause desensitization to neurogenic inflammation, to chemically and thermally induced pain, and to responses involving sensory afferent pathways including C-fibers and the hypothalamic temperature control region. The induced desensitization may have application to arthritis, asthma, allergic responses, fever, pain associated with cancer or Herpes virus infection, and in biological processes mediated by substance P or other neuropeptides depleted by capsaicin treatment.

As indicated above, resiniferatoxin has similar effects to capsaicin, but differs in its much greater potency - up to $10^4$, which should remarkably reduce non-specific binding and permit detection of receptors against the background on non-specific binding. RTX, TTX and cogeners thereof also show a somewhat different spectrum of action, enabling greater desensitization at a given level of systemic toxicity and greater desensitization relative to acute induction of pain.

Moreover, desensitization by resiniferatoxin and congeners thereof can be activated by topical, intravenous, intraperitoneal, oral, and subcutaneous administration. Labelled RTX, and congeners thereof may be administered by these modes of administration to an animal or subject such as a mammal (e.g., mouse, rat or human).

Furthermore, it should be noted that capsaicin exerts its actions on all mammals examined, but not on birds and low vertebrates (Monsereenusorn et al. (1982) *CRC Crit. Rev. Toxicol.*, Vol. 10, p. 321–339). Based on the resemblances in the activities of capsaicin, resiniferatoxin, TTX and the compounds of the invention documents in this application, it is extrapolated that the effects of RTX are not limited to rats and mice but extend to man as well.

Labelled RTX and congeners thereof can be made into pharmaceutical compositions by combination with appropriate medical carriers or diluents. For example, labelled RTX, TTX or congeners thereof can be dissolved in oils, propyleneglycol or other solvents commonly used to prepared injectable solutions. Suitable carriers include physiological saline, polyethylene glycol, ethanol, sesame oil, cremophor and isopropyl myristate. For topical application, labelled RTX or congeners thereof can be formulated as an ointment or cream.

The following methods and excipients are merely exemplary and in no way limit the invention.

The labelled compounds of the present invention (including RTX and TTX) in pharmaceutical dosage forms may be used in the form of their labelled pharmaceutically acceptable salts, and also may be used alone or in appropriate association, as well as in combination with other pharmaceutically active compounds.

The labelled compounds of the present invention may be formulated into preparations for injections by dissolving, suspending, or emulsifying them in aqueous solvents such as normal saline, Dextrose 5%, or non-aqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The labelled compounds of the invention may be combined with other compounds having the desired effect.

The desirable dose of the labelled compounds of the present invention varies with the subject, drug form, method and period of administration. However, in order to obtain desirable effects for in vivo administration, generally it is recommended to administer $0.1\times10^{-3}$ to 10 mg/kg, preferably $0.1\times10^{-3}$ to 0.1 mg/kg, body weight of the labelled compounds of the present invention for single application, or less upon multiple application. In terms of composition, labelled compounds should be present between 0.0001 to 10% by weight, preferably 0.0001 to 1% by weight.

For the measurement of binding in vitro. the labelled compounds should be present in the binding mixture at a concentration of between $10^{-13}$ M to $10^{-6}$ M, preferably $10^{-11}$ M to $10^{-8}$ M. For storage and dilution, the compounds may be more concentrated, preferably at least 100-fold more concentrated, and concentrations of 1 M or greater are acceptable. Suitable solvents before addition to the assay mixture include dimethylsulfoxide, ethanol or methanol. For storage, these solvents or mixtures with less non-polar solvents such as ethyl acetate are suitable.

The present invention may be useful to demonstrate specific capsaicin receptors, as well as to evaluate synthetic capsaicinoids, to screen for novel natural products acting on these receptors, and to assay concentrations and amounts of such compounds. The invention represents the first binding assay for capsaicin/-resiniferatoxin receptors.

Accordingly, one use of the labelled compounds of the invention is the characterization of specific receptor binding.

Another use of the labelled compounds of the invention is as an alternative to animal testing for the evaluation of vanilloid structure-activity relations. The above receptor assay is performed at a fixed concentration of labelled RTX or labelled congener and at increasing concentrations of the vanilloid in a competition assay as described above. The assay would find application in the detailed evaluation of the many vanilloid derivatives produced by the pharmaceutical industry in its attempts to develop unique vanilloids as therapeutic agents. The assay has the advantage of being less expensive than animal testing; it avoids the ethical issue of using live animals in drug evaluation; and it possesses the important advantage that quantification is not confused by problems of drug absorption and stability.

A further application of the present invention is for screening tissue extracts for potential endogenous compounds interacting at the capsaicin receptor. The tissue is extracted by any of a variety of methods obvious to one skilled in the art. Examples include extraction with methanol or 1N HCl followed by drying. The extracts are then assayed in the binding assay as described above.

The present invention is further directed to screening of natural products for other structural classes of compounds which interact at the capsaicin receptor. The natural sources, e.g., plants, marine animals, or fungi, are extracted by any of a variety of methods obvious to one skilled in the art. Examples include extraction with methanol or 1N HCl followed by drying. The extracts are then assayed in the binding assay as described above.

Quantification of the levels of natural products or endogenous compounds represents another use of the labelled compounds of the present invention. The natural products are assayed quantitatively by competition as described above, and the concentrations giving competition are compared and evaluated from standard competition curves with known amounts of known compounds.

Moreover, the invention may be used for the quantification of the levels specifically of capsaicin and capsaicin analogs. Prior art methodology requires the determination separately of each capsaicin analog. The current method provides an integrated evaluation of the sum of all such analogs in a single determination. This might have utility in the spice industry.

The present invention may be further directed to the localization of receptors to specific cells or tissue regions. This will have application in at least three areas. It will be valuable in research studies. It will permit quantitation of the level of functional activity of the capsaicin sensitive pathways. It will permit isolation of cells containing capsaicin receptors. The latter is essential for cloning of the capsaicin receptors and the development of assays selective for putative receptor subclasses.

The following Examples are intended to illustrate the claimed invention and will enable others skilled in the art to understand the invention more completely. However, the invention should not be interpreted as being limited to only these representative examples.

EXAMPLE 1

This Example describes the synthesis of a compound of the invention.

The synthesis of $^3$H-resiniferatoxin is adapted from W. Adolf, et al., *Journal of Natural Products*, 45, 348 (1982). However, the procedure of Adolf et al is modified as described below.

[$^3$H] Homovanillic acid in ethanol (Amersham, 2 Ci, 38 Ci/mmoL, prepared by catalytic hydrogenation of 3-bromo homovanillic acid (Transworld Chemicals, Rockville, MD) with tritium gas) calculated to contain 9.6 mg ([$^3$H] homovanillic acid), is evaporated to dryness under $N_2$, and three times redissolved in acetonitrile and evaporated to dryness to remove traces of ethanol. The original solution is colorless and the TLC is good but after the above treatment the solution is discolored and the TLC shows slight streaking.

Resiniferonol orthophenylacetate (22.3 mg) is three times dissolved in anhydrous pyridine and evaporated to dryness. N-Methylfluoropyridinium tosylate (25 mg) (prepared by refluxing equimolar amounts of 2-fluoropyridine and methyl p-toluenesulfonate overnight in anhydrous toluene; the filtered solid is hygroscopic and is quickly dried in vacuum) is added, plus 0.25 ml of a solution of methylene chloride (5 ml, distilled from $P_2O_5$) and 0.14 ml of triethylamine (distilled from phenyl isocyanate). After one-half hour the mixture is evaporated to dryness, the flask is covered with a septum, flushed with $N_2$, and 0.25 ml of a solution of benzene (2 ml, distilled from Na) and triethylamine (0.17 ml) is added, followed by the labelled homovanillic acid in 0.25 ml of acetone (dried over molecular sieves). After stirring 1.5 hours at 60° C. the mixture is taken up in phosphate buffer (pH 7.5) and extracted 5 times with ethyl acetate.

The combined extracts ar dried over $Na_2SO_4$, filtered and evaporated. The black tarry mass is chromatographed on a $SiO_2$ column. The first fraction ($Et_2O$-hexane), 4:1) is evaporated and the residue injected into a Magnum C-18 HPLC column (70% MeOH-$H_2O$) and the product peak collected. The solution of product appears chemically pure by HPLC and radiologically pure by counting fractions from the HPLC column. The solution (54 ml) contains 44.4 mCi of activity, or 0.82 mCi/ml.

Alternative routes to the method of Example 1 for synthesizing labelled compounds of the invention will be described hereinbelow.

In lieu of radiolabelled resiniferatoxin, biologically active congeners of resiniferatoxin can be radiolabelled by the same synthetic route. Such congeners will have the general structure:

where $R_3$ is OH, X is 0 or 1, $R_1$, $R_2$, $R_4$ and $R_5$ each are: H, OH $OC(CH_2)_nH$, $O(CH_2)_nH$ with n=0 to 10.

In labelled compounds of the above congeners, at least one of $R_1$, $R_2$, $R_4$ or $R_5$ is labelled, for instance, with $^3$H, $^{125}$I $^{131}$I. In this formula, one or more of $R_1$, $R_2$, $R_4$ and $R_5$ is [$^3$H]. $R_3$ should be OH so that the derivative is active.

EXAMPLE 2

This example describes the synthesis of radiolabelled tinyatoxin.

Example 1 is repeated, except that the compound to be prepared is radiolabelled tinyatoxin, which has the structure:

where R is and which can be prepared in the same manner as for resiniferatoxin, except using phenylacetic acid in place of homovanillic acid.

EXAMPLE 3

For any of the congeners of the invention, an alternative route for labeling (e.g., at [20—$^3$H]) is to prepare [20—$^3$H] resiniferonol 9,13,14-orthophenylacetate from resiniferonol 9,13,14-orthophenylacetate by oxidation at C20 with manganese dioxide and reduction with tritiated borohydride as described by Kreibich and Hecker, Z. Naturforsch. 74, 448-456, 1970. The [$^3$H] resiniferanol 9,13,14-orthophenylacetate is then esterified with homovanillic acid by standard techniques (W. Adolf et. al., J. Natural Products, 45, 348 (1982)) to produce [$^3$H] resiniferatoxin, with p-hydroxyphenylacetic acid to produce [$^3$]tinyatoxin, or with an appropriately substituted phenylacetate derivative to yield the corresponding [$^3$H]resiniferatoxin analog.

EXAMPLE 4

For resiniferatoxin, tinyatoxin, and congeners thereof possessing an unsubstituted m-hydrogen on the substituted phenylacetic acid side chain, $^{125}$I or $^{131}$I labelled compounds can be prepared by iodination using chloramine T or using glucose oxidase or lactoperoxidase. (W.M. Hunter et al., (1962) Nature 194, 495-496.) One or more of $R_1$, $R_2$, $R_4$ and $R_5$ may be $^{125}$I or $^{133}$I in the compounds of the invention. These derivatives have the advantage of greater specific activity than the [$^3$H] labelled derivatives, permitting detection of smaller amounts of receptor or permitting assay of the receptors at lower ligand concentrations. These latter conditions are significant, because they permit a more distortion free measurement of potencies of ligands at the receptor.

EXAMPLE 5

For resiniferatoxin, tinyatoxin, and its congeners, the compounds can be labelled by reduction at C15, 16 with tritium gas using a sterically hindered reduction catalyst. The product of the reduction is [16, 17-$^3$H]dihydroresiniferatoxin or the corresponding dihydro derivative of an RTX congener.

EXAMPLE 6

[$^3$H]RTX (37 Ci/mmol) is synthesized by esterification of resiniferonol 9,13,14-orthophenylacetate (Chemicals for Cancer Research, Inc., Chaska, MN) at the C20 position with [$^3$H]homovanillic acid (Chemical Synthesis and Analysis Laboratory, NCI-FCRF, Frederick, MD). The labelled compound is purified on HPLC and cochromatographed with authentic RTX (Chemicals for Cancer Research, Inc., Chaska, MN). The biological activity of [$^3$H]RTX is confirmed in 2 assays: induction of hypothermia in CD-1 mice ($10^{-5}$ g/kg s.c.) and induction of ear edema in Sprague-Dawley rats ($2 \times 10^{-7}$ g/ear).

Capsaicin is from Polysciences (Warrington, PA). Dihydrocapsaicin, piperine, epinephrine, norepinephrine, L-DOPA, dopamine, ruthenium red and phorbol 12,13-dibutyrate (PDBu) are purchased from Sigma (St.Louis, MI). Zingerone is from Pflatz and Bauer (Waterbury, CT).

Membrane preparations are obtained from the DRG and Gasser ganglia of female Sprague-Dawley rats (250-300 g); animals are sacrificed by decapitation under ether anesthesia, the ganglia removed and collected into ice-cold disrupting buffer (5 mM KCl, 5.8 mM NaCl, 2 mM MgCl$_2$, 12 mM glucose, 137 mM sucrose, 10 mM HEPES, 5 mM DTT, 2 mM EGTA, pH 7.4). After homogenization with the aid of a Polytron tissue homogenizer, samples are filtered over surgical gauze and then washed twice with the same buffer and stored at −70° C. Particulate fractions are obtained from other rat neural tissues (cerebellum, spinal cord, preoptic region, striatum, substantia nigra) and from DRG of pigs (Mt. Airy Locker Co., Mt. Airy, MD), sheep, cows (kindly provided by Dr. Solomon, USDA, Beltsville, MD), and chickens (Truslow Farms, Chesterton, MD) by a similar procedure.

Subcellular fractions are prepared by a modification of the method of Bastiaensen et al. (Bastiaensen, E., Miserez, B. and De Potter, W., Subcellular fractionation of bovine ganglion stellatum: co-storage of noradrenaline, Met-enkephalin and neuropeptide Y in large 'dense-cored' vesicles, Brain Res., 442 (1988) 124–130.) Briefly: DRG are dissected free from capsule, cut into small pieces with scissors, and then homogenized with a teflon pestle (20 strokes) in ice-cold 0.25 M sucrose/ 20 mM Tris-Cl (pH 7.4) buffer. The homogenate is filtered over surgical gauze; it is then centrifuged for 10 min at 2000 $g_{max}$, giving a pellet $P_1$, and again at 10 000 $g_{max}$ for 15 min giving a pellet $P_2$. The $P_1$ and $P_2$ pellets are saved as nuclear and mitochondrial fractions for binding studies. The resulting supernatant is further centrifuged at 50 000 $g_{max}$ for 60 min, and then the pellet is harvested as the plasma-membrane enriched microsomal fraction.

The binding assays are carried out in a volume of 250 ul, containing assay buffer (same as the disrupting buffer but omitting DTT and EGTA and including 0.75 mM $CaCl_2$), 26–30 ug of membrane protein and 0.25 mg/ml bovine serum albumin. Both labelled RTX and nonradioactive ligands are added in EtOH at a maximal concentration of 0.1%; this solvent concentration does not effect binding. Tubes are kept on ice while the additions are made. The assay mixture is incubated for 10 min at 37° C.; it is then cooled on ice. 150 ul of the mixture is pipetted onto Whatman GF/C or GF/F glass fiber filters presoaked with 10 mg/ml bovine serum albumin in 20 mM Tris-Cl (pH 7.4) and filtered immediately. An aliquot of 50 ul of the mixture is removed to determine total radioactivity. The filters are washed with 100 ml of ice-cold 20 mM Tris-Cl, pH 7 4, containing 0.1 mg/ml bovine serum albumin, and the bound radioactivity is determined by scintillation counting. Non-specific binding is determined in the presence of 100–1000 nM non-radioactive RTX. Under these conditions approximately 30% of the non-specific binding is due to sticking of [$^3$H]RTX to the filters. The remainder presumably reflects partitioning into the lipid phase of the membranes, as had been observed previously for typical phorbol esters (Driedger, P.E. and Blumberg, P.M., Specific binding of phorbol ester tumor promoters, Proc. Natl. Acad. Sci. U.S.A., 77 (1980) 567–571).

Binding data from saturation experiments using increasing concentrations of hot ligand are analyzed using the collection of computer programs described by McPherson (McPherson, G.A., Analysis of radioligand binding experiments: a collection of computer programs for the IBM PC, J.Pharmacol.Methods, 14 (1985) 213–228).

Scatchard and Hill transformations are performed by the Equilibrium Binding Data Analysis program referred to as EBDA. Data are further analyzed by the curvilinear regression program LIGAND (Munson, R.J. and Rodbard, D., LIGAND: a versatile computerized approach for characterization of ligand-binding systems, Anal.Biochem, 107 (1980) 220–239).

RTX binding is also analyzed in the presence of a fixed, low (60 pM or 300 pM) concentration of [$^3$H]RTX and increasing concentrations of non-radioactive RTX or other ligand. The concentration of non-radioactive ligands producing 50% inhibition ($IC_{50}$) of [$^3$H]RTX binding is determined by a program fitting a theoretical sigmoidal competition curve to the data.

The $K_i$ value for RTX is calculated from the relationship $K_i = ID_{50}$-L; the $K_i$ values for other ligands are calculated from the general form of the equation (Cheng, Y.C. and Prusoff, W.H., Relation between the inhibition constant ($K_i$) and the concentration of inhibitor which causes 50 per cent inhibition ($I_{50}$) of an enzymatic reaction, Biochem. Pharmacol., 22 (1973) 3099–3108) $K_i = IC_{50}/(1+L/K_d)$ where L=concentration of labelled ligand and $K_d$=dissociation constant of radioactive ligand as determined in the saturation experiments using variable concentrations of hot ligand. Comparison of the quality of fit using single and multiple site competition models is performed by the LIGAND program.

In place of membrane preparations from dorsal root ganglia, membrane preparations from the dorsal horn of the spinal cord can also be used.

Figure 1A:
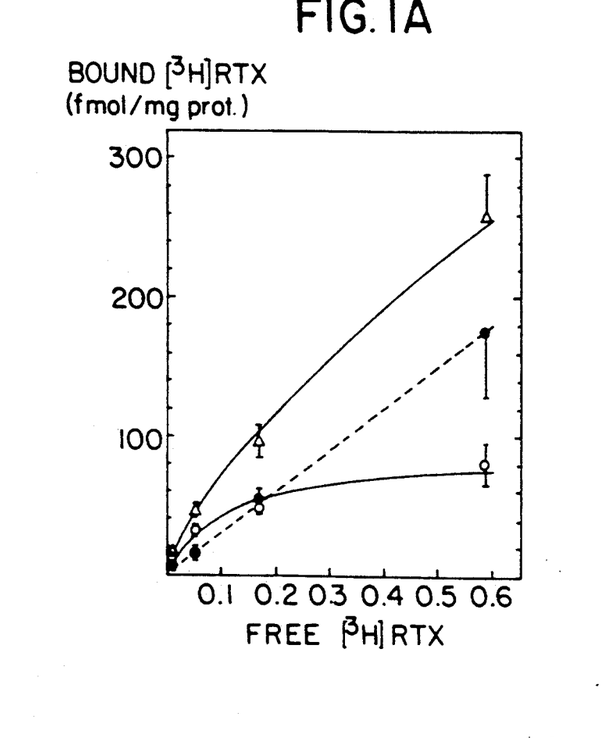
Figure 1B:
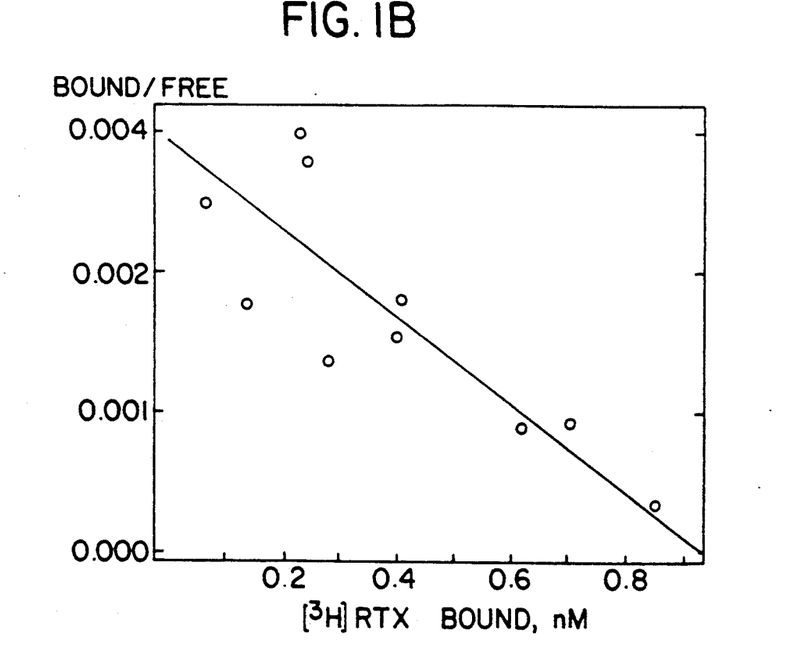

[$^3$H]RTX binding is examined using membrane preparations from dorsal root ganglia (DRG) of female Sprague-Dawley rats. DRG are chosen because of their high density of capsaicin-sensitive neurons (Marsh, S.J., Stansfeld, E., Brown, D.A., Davey, R. and McCarthy, D., The mechanism of action of capsaicin on sensory C-type neurons and their axons in vitro, Neuroscience, 23 (1987) 275–289; Wood, J.N., Winter, J., James, I.F., Rang, H.P., Yeats, J. and Bevan, S., Capsaicin-induced ion fluxes in dorsal root ganglion cells in culture, J. Neuroscience, 8 (1988) 3208–3220). [$^3$H]RTX display specific, saturable binding to the DRG membranes (FIG. 1A). Non-specific binding, which is defined as that occurring in the presence of 100–1000 nM non-radioactive RTX, is linear with the concentration of the labelled compound. Scatchard analysis of the data cumulated from 3 separate determinations is consistent with a single component possessing a $K_d$ of 300 pM and a $B_{max}$ of 150 fmol/mg protein. The Hill coefficient is 0.96. At the $K_d$ specific binding represented approximately 50% of the total. The curvilinear analysis of the data confirms the one site model suggested by the Scatchard plot and gives final parameter estimates of $K_d = 270$ pM and $B_{max} = 160$ fmol/mg protein (FIG. 1B).

Figure 1C:
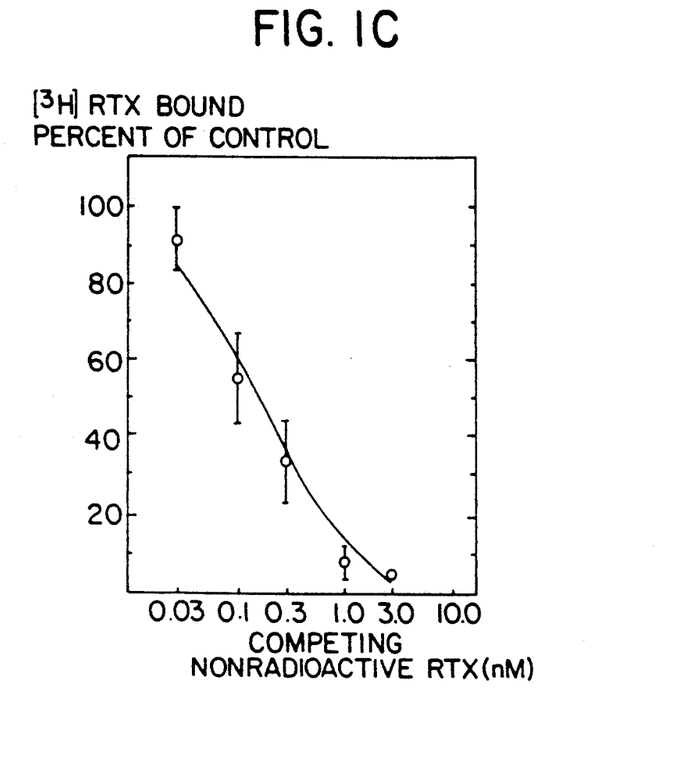

Because of the relatively high non-specific binding, the direct binding data is compared with that for competition of [$^3$H]RTX by non-radioactive RTX. Using a concentration of [$^3$H]RTX below the $K_d$ (60 pM radioactive ligand) and non-radioactive RTX over the concentration range of 30 pM to 3 nM, a $K_i$ of 110±40 pM (mean±SEM, 3 determinations; FIG. 1C) is obtained. LIGAND analysis of the data confirms that the one site fit is statistically superior to the two site fit of the data.

Figure 2:
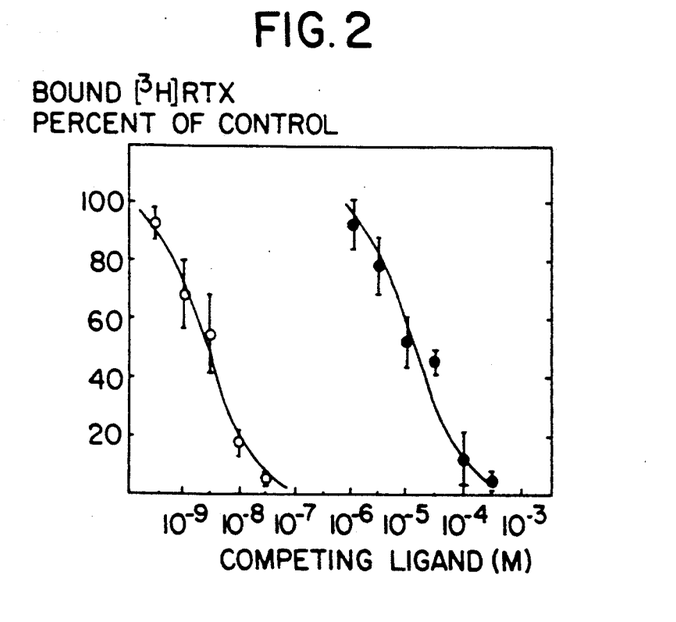
FIG. 2. Dose-response curves for inhibition of [$^3$H]RTX binding to membrane preparations from pig DRG by nonradioactive RTX (O) and capsaicin (●). Each point represents the mean of 3 experiments. Error bars indicate SEM.

Rat DRG membranes are chosen for the binding analysis because of the data available on the biological effects of RTX in this system. A disadvantage, however, is the small amount of material obtainable per rat. Therefore, [$^3$H]RTX binding to membranes of DRG from large mammals is examined. Specific binding is observed in DRG from sheep, cows, and pigs. Pigs are chosen for further experiments because of availability. The proportion of specific to total binding is somewhat lower in the pig DRG than is the case in the rat. Nonetheless, using inhibition of a fixed, low concentration of [$^3$H]RTX with non-radioactive RTX, a $K_i$ of 2.4±0.3 nM (mean±SEM, 4 determinations) is obtained, significantly higher than that obtained in the rat (FIG. 2). The $B_{max}$, 730±80 fmol/ mg protein (mean±SEM, 4 determinations), is also greater. The LIGAND analysis yielded a $K_i$ of 2.2 nM and provided the best fit with the one site model. Although the effects of capsaicin have not been determined in the pig, significant differences in the sensitivities of different species to capsaicin have been reported (Jancso, N., Desensitization with capsaicin and related acylamides as a tool for studying the function of pain receptors, In Pharmacology of pain, Vol. 9, Pergamon Press, Oxford, 1968, pp. 33–55; Szolcsanyi, J., Capsaicin type pungent agents producing pyrexia, In A.S. Milton (ed.), Handbook of Experimental Pharmacology, Vol. 60, Springer-Verlag, Berlin, Heidelberg, 1982, pp. 437–478) The values obtained by competition are confirmed by Scatchard analysis of partially purified membrane preparations (see below) ($K_d=1.7$ nM, $B_{max}=700$ fmol/mg protein; data from 2 separate determinations are analyzed by the LIGAND program; Hill coefficient =0.9, best fit for single site model).

Binding is routinely measured using an incubation time of 10 min at 37° C. Time course experiments using pig DRG membranes indicate that specific binding is maximal at this time and decline thereafter. Addition of an excess of non-radioactive RTX causes complete loss of specific binding by 10 min at 37° C., indicating rapid equilibration.

Alternatively, binding can be measured to membrane preparations from dissected dorsal horn from pig spinal cord. The $K_d$ is then 0.1 nM and the % specific binding is 90%

The biochemical specificity of [$^3$H]RTX binding is confirmed using three approaches. First, heating of pig DRG membranes to 55° C. for 10–20 min completely inactivates specific [$^3$H]RTX binding (2 experiments). Second, the [$^3$H]RTX binding shows appropriate neural localization. Gasser ganglia represents the central homolog of the dorsal root ganglia. [$^3$H]RTX bound to particulate preparations from rat Gasser ganglia with similar $K_d$ and $B_{max}$ ($K_d=130$ pM, $B_{max}=90$ fmol/mg; data from 3 separate experiments are analyzed by the LIGAND program; Hill coefficient =0.87, best fit for 1 site model) to that observed for rat DRG. Conversely, no specific binding is observed for rat cerebellum, a neural tissue reported not to be affected by capsaicin (Jancso, G. and Wollemann, M., The effect of capsaicin on the adenylate cyclase activity of rat brain, Brain Res., 123 (1977) 323–329). Detection of [$^3$H]RTX binding in rat brain preoptic region, striatum and substantia nigra, is also very difficult. These latter areas have been implicated in capsaicin action, although the magnitude of the effects has been smaller (Hajos, M., Engberg, G., Nissbrandt, H., Magnusson, T. and Carlsson, A., Capsaicin-sensitive vasodilatatory mechanisms in the rat substantia nigra and striatum, J. Neural Transmission, 74 (1988) 129–139; Jancso, G. and Wollemann, M., The effect of capsaicin on the adenylate cyclase activity of rat brain, Brain Res., 123 (1977) 323–329). Perhaps these negative results reflect the detection limit of the current binding methodology. Thirdly, binding is not detected in DRG from chickens, in contrast to the results described above for mammals, in agreement with birds being unresponsive to the pungent activity of capsaicin (Jancso, N., Desensitization with capsaicin and related acylamides as a tool for studying the function of pain receptors, In Pharmacology of pain, Vol. 9, Pergamon Press, Oxford, 1968, pp. 33–55).

The pharmacological specificity of [$^3$H]RTX binding is examined for three classes of compounds—capsaicin and its analogs, phorbol-related activators of protein kinase C, and catecholamines. Capsaicin inhibits specific [$^3$H]RTX binding to pig DRG (FIG. 2). The $K_i$ is 14±2 uM (mean±SEM in 3 determinations), indicating a $6\times10^3$ fold lower potency than RTX. This difference in potency agrees well with the $10^3$-$10^4$-fold difference in potencies for induction of hypothermia or neurogenic inflammation (Szallasi, A. and Blumberg, P.M., Resiniferatoxin, a phorbol-related diterpene, acts as an ultrapotent analog of capsaicin, the irritant constituent in red pepper, Neuroscience, 30 (1989) 515–520). Similar inhibition is observed for rat DRG ($K_i=7\pm2$ uM; mean±SEM in 3 determinations) and Gasser ganglia preparations ($K_i=8\pm4$ uM; mean±range in 2 determinations). At 30 uM, dihydrocapsaicin, a derivative with similar potency to capsaicin (Hayes, A.G., Oxford, A., Reynolds, M., Shingler, A.H., Skingle, M., Smith, C. and Tyers, M.B., The effects of a series of capsaicin analogs on nociception and body temperature in the rat, Life Sci., 34 (1984) 1241–1248), inhibits to a similar degree as does capsaicin (Table 1). Piperine and zingerone, less potent analogs (Szolcsanyi, J., Capsaicin type pungent agents producing pyrexia, In A.S. Milton (ed.), Handbook of Experimental Pharmacology, Vol. 60, Springer-Verlag, Berlin, Heidelberg, 1982, pp. 437–478), does not inhibit or does so more weakly (Table 1). Catecholamines possess some homology to the 3-methoxy, 4-hydroxyphenyl moiety in RTX. At 100 uM, epinephrine, norepinephrine, and L-DOPA (1 experiment each) or dopamine (3 experiments) does not compete for [$^3$H]RTX binding sites in pig DRG.

The side chain at C20 is essential for the capsaicin-like activity of RTX (Szallasi, A., Sharkey, N.A. and Blumberg, P.M., Structure-activity analysis of resiniferatoxin analogs, Phytotherapy Res., 6: 253–257, 1990). Specific [$^3$H]RTX binding is inhibited neither by resiniferonol 9,13,14-orthophenylacetate, the C20-deesterified analog of RTX, nor by phorbol 12,13-dibutyrate, the typical ligand used for analysis of binding to protein kinase C (Table 1). Conversely, RTX inhibits specific [$^3$H]phorbol 12,13-dibutyrate binding to protein kinase C in the rat DRG preparations only at uM concentrations.

Ruthenium red fails to inhibit [$^3$H]RTX binding at biologically effective concentrations (Table I).

TABLE 1

Pharmacological specificity of [$^3$H]RTX binding

| | rat DRG[1] | pig DRG[1] |
|---|---|---|
| 1. Phorbol esters | | |
| PDBu[2,3], 200 nM | 106 ± 9 (n = 3) | 100 ± 2 (n = 3) |
| ROA[4], 200 nM | 106 (n = 2) | NT |
| 2 μM | NT | 105 ± 6 (n = 4) |

| | rat Gasser gg[1] | pig DRG[1] |
|---|---|---|
| 2. Capsaicinoids | | |
| capsaicin, 30 μM | 30 ± 11 (n = 3) | 28 ± 4 (n = 4) |
| dihydrocapsaicin, 30 μM | 22 (n = 2) | 33 ± 5 (n = 3) |
| piperine, 30 μM | 118 (n = 2) | 109 ± 2 (n = 3) |
| zingerone, 30 μM | 111 (n = 1) | 92 ± 7 (n = 3) |
| 3. Ruthenium Red, 10 μM | | 109 (n = 2) |

[1] % of specific [$^3$H]RTX binding measured in the absence of the tested compound ± SEM
[2] phorbol 12,13-dibutyrate
[3] $K_d$ for [$^3$H]PDBu binding to membrane preparations from rat and pig DRG is 8.5 nM and 11.5 nM, respectively
[4] resiniferonol 9,13,14-orthophenylacetate
n = number of experiments; each value is determined in each experiment at least in triplicate.

Treatment of adult rats with RTX or capsaicin causes desensitization, with profound morphologic effects on the target neurons in rat DRG (Joo, F., Szolcsanyi, J. and Jancso-Gabor, A., Mitochondrial alterations in the spinal ganglion cells of the rat accompanying the long-lasting sensory disturbance induced by capsaicin, Life Sci., 8 (1969) 621–626; Szallasi, A., Joo, F. and Blumberg, P.M., Duration of desensitization and ultrastructural changes in dorsal root ganglia in rats treated with resiniferatoxin, an ultrapotent capsaicin analog, Brain Res., 503 (1989) 68–72). Although desensitization is expressed within 1–4 hrs in rats treated with 300 ug/kg RTX s.c. (Szallasi, A. and Blumberg, P.M., Resiniferatoxin, a phorbol-related diterpene, acts as an ultrapotent analog of capsaicin, the irritant constituent in red pepper, Neuroscience, 30 (1989) 515–520; Szallasi, A., Joo, F. and Blumberg, P.M., Duration of desensitization and ultrastructural changes in dorsal root ganglia in rats treated with resiniferatoxin, an ultrapotent capsaicin analog, Brain Res., 503 (1989) 68–72.) RTX binding is similar to controls for DRG preparations obtained 12 hr after such RTX treatment.

In preliminary studies, porcine DRG are subjected to subcellular fractionation according to the method of Bastiaensen et al.(Bastiaensen, E., Miserez, B. and De Potter, W., Subcellular fractionation of bovine ganglion stellatum: costorage of noradrenaline, Met-enkephalin and neuropeptide Y in large 'dense-cored' vesicles, Brain Res., 442 (1988) 124–130). This procedure yield fractions corresponding to mitochondria, microsomal/plasma membrane, and nuclear pellet. No specific [$^3$H]RTX binding is found in the nuclear pellet. Specific [$^3$H]RTX binding is 5-fold higher in the microsomal/plasma membrane fraction than in the mitochondrial fraction using a fixed (300 pM) concentration of the radioactive ligand.

The selectivity of capsaicin action and the fairly strict structural requirements for capsaicin-like activity suggests that capsaicin interacts at specific receptors to produce its effects (Hayes, A.G., Oxford, A., Reynolds, M., Shingler, A.H., Skingle, M., Smith, C. and Tyers, M.B., The effects of a series of capsaicin analogs on nociception and body temperature in the rat, Life Sci., 34 (1984) 1241–1248; Jancso, N., Desensitization with capsaicin and related acylamides as a tool for studying the function of pain receptors, In Pharmacology of pain, Vol. 9, Pergamon Press, Oxford, 1968, pp. 33–55; Szolcsanyi, J., Capsaicin type pungent agents producing pyrexia, In A.S. Milton (ed.), Handbook of Experimental Pharmacology, Vol. 60, Springer-Verlag, Berlin, Heidelberg, 1982, pp. 437–478). Additional indirect evidence for the existence of capsaicin binding sites is found by using capsaicin-like photoaffinity probes (James, I.F., Walpone, C.S.J., Hixon, J., Wood, J.N. and Wrigglesworth, R., Long-lasting activity produced by a capsaicin-like photoaffinity probe, Mol.Pharmacol., 33 (1988) 643–649), but attempts to identify receptors for capsaicin by use of radiolabelled capsaicin have not been successful. The present inventors have found specific, saturable binding of RTX, an ultrapotent capsaicin analog, to membranes prepared from sensory (dorsal root and Gasser) ganglia of various species. The evidence that the specific [$^3$H]RTX binding represents the postulated capsaicin receptor includes its pharmacological specificity, its tissue specificity, and its species specificity.

A minor weakness in the analysis is the level of non-specific binding in the assay. This background limits our present ability to detect [$^3$H]RTX binding in the central nervous system. Given the effect of intrathecally injected capsaicin in thermoregulation (Jancso, N., Desensitization with capsaicin and related acylamides as a tool for studying the function of pain receptors, In Pharmacology of pain, Vol. 9, Pergamon Press, Oxford, 1968, pp. 33–55), and in vasoregulation (Hajos, M., Engberg, G., Nissbrandt, H., Magnusson, T. and Carlsson, A., Capsaicin-sensitive vasodilatatory mechanisms in the rat substantia nigra and striatum, J. Neural Transmission, 74 (1988) 129–139), receptors in the central nervous system would be predicted. The background also complicates efforts to demonstrate subclasses of capsaicin receptors. Comparison of relative potencies of RTX and capsaicin (deVries, D.J. and Blumberg, P.M., Thermoregulatory effects of resiniferatoxin in the mouse: comparison with capsaicin, Life Sci., 44 (1989) 711–715; Szallasi, A. and Blumberg, P.M., Resiniferatoxin, a phorbolrelated diterpene, acts as an ultrapotent analog of capsaicin, the irritant constituent in red pepper, Neuroscience, 30 (1989) 515–520), as well as structure-activity analysis of RTX (Szallasi, A., Sharkey, N.A. and Blumberg, P.M., Structure-activity analysis of resiniferatoxin analogs, Phytotherapy Res., 6:253–257, 1990) and capsaicin analogs (Hayes, A.G., Oxford, A., Reynolds, M., Shingler, A.H., Skingle, M., Smith, C. and Tyers, M.B., The effects of a series of capsaicin analogs on nociception and body temperature in the rat, Life Sci., 34 (1984) 1241–1248; Jancso, N., Desensitization with capsaicin and related acylamides as a tool for studying the function of pain receptors, In Pharmacology of pain, Vol. 9, Pergamon Press, Oxford, 1968, pp. 33–55; Szolcsanyi, J., Capsaicin type pungent agents producing pyrexia, In A.S. Milton (ed.), Handbook of Experimental Pharmacology, Vol. 60, Springer-Verlag, Berlin, Heidelberg, 1982, pp. 437–478), strongly suggests the existence of pharmacologically differentiable subclasses of capsaicin targets.

The nature of the capsaicin receptor remains unknown. A prominent feature of capsaicin desensitization of DRG neurons is swelling of mitochondria (Joo, F., Szolcsanyi, J. and Jancso-Gabor, A., Mitochondrial alterations in the spinal ganglion cells of the rat accompanying the long-lasting sensory disturbance induced by capsaicin, Life Sci., 8 (1969) 621–626), and the mitochondrial NADH-Coenzyme Q oxidoreductase has been reported to be inhibited at high capsaicin concentrations (Shimomura, Y., Kawada, T. and Suzuki, M., Capsaicin and its analogs inhibit the activity of NADH-Coenzyme Q oxidoreductase of the mitochondrial respiratory chain, Arch. Biochem. Biophys., 270 (1989) 573–577) In contrast, the preliminary fractionation of the DRG particulate fraction suggests localization of [$^3$H]RTX binding in the microsomal/plasma membrane fraction. Our results are thus consistent with the weak evidence suggesting that the capsaicin receptor might represent a ligand-gated cation channel (Marsh, S.J., Stansfeld, E., Brown, D.A., Davey, R. and McCarthy, D., The mechanism of action of capsaicin on sensory C-type neurons and their axons in vitro, Neuroscience, 23 (1987) 275–289). This concept has gained further support by showing that ion fluxes evoked by RTX in cultured DRG neurons cross-desensitized with those evoked by capsaicin (Winter, J., Dray, A., Wood, J.N. and Bevan, S.J., Resiniferatoxin is a potent capsaicin-like sensory neurotoxin, Soc. Neurosci. Abstr., 18 (1989) 176.8).

RTX binding is similar for controls and for DRG preparations obtained 12 hr after in vivo RTX desensitization. Moreover, ruthenium red, an agent known to block capsaicin desensitization (Maggi, C.A., Patacchini, R., Santicoli, P., Giuliani, S., Geppetti, P. and Meli, A., Protective action of Ruthenium red toward capsaicin desensitization of sensory fibers, Neurosci. Lett., 88 (1988) 201-205), fails to compete for RTX binding sites. Our results indicate that acute desensitization does not represent a direct effect of the receptor loss. The present inventors have found a different picture in neonatally treated animals, where loss of neurons is coupled with a very significant loss of [$^3$H]RTX binding sites (Szallasi et al., manuscript in preparation).

Our demonstration of specific [$^3$H]RTX binding provides a new opportunity for the analysis of the biochemical mechanism of action of capsaicin. It further may allow dissection of possible subclasses of capsaicin responses, as suggested by in vivo structure activity analysis. Characterization and mechanistic understanding of the basis of these subclasses will be of great importance for the therapeutic development of this class of agents. Capsaicin has already been used in human therapy; e.g. in the treatment of diabetic neuropathy (Ross, D.R. and Varipapa, R.J., Treatment of painful diabetic neuropathy with topical capsaicin, The New England Journal of Medicine, 321 (1989) 474–475), post-mastectomy pain syndrome (Watson, C.P.N., Evans, R.J. and Watt, V.R., The post-mastectomy pain-syndrome and the effect of topical capsaicin, Pain, 38 (1989) 177–186), and post-herpetic neuralgia (Watson, C.P.N., Evans, R.J. and Watt, V.R., Post-herpetic neuralgia and topical capsaicin, Pain, 33 (1988) 333–340), and commercial capsaicin creams are available (Zostrix, GenDerm Corp. and Axsain, Galen Pharma.).

Finally, inhibition of [$^3$H]RTX binding provides a potential assay for detecting potential endogenous analogs of capsaicin if such exist.

Accordingly, the results demonstrate specific binding of [$^3$H]RTX to particulate preparations from dorsal root ganglia (DRG) and spinal cord, target tissues of both RTX and capsaicin action. The $K_d$ is 0.27 nM for DRG from the rat; the $B_{max}$ is 160 fmol/mg. The respective values for pig DRG are 2.2 nM and 730 fmol/mg Typical phorbol esters do not inhibit [$^3$H]RTX binding. Capsaicin inhibits binding with $10^4$-fold lower affinity than RTX, consistent with the relative in vivo potencies. The specific [$^3$H]RTX binding appears to represent the postulated capsaicin receptor.

EXAMPLE 7

Resiniferonol 9, 13, 14-orthopehnylacetate is coupled with 2,5-dinitro-3-hydroxyphenylacetic acid by the method of W. Adolf et al., J. Natural Products, 45, 348 (1982) in order to make a fluorescently labelled compound of the invention.

EXAMPLE 8

2 mg of the radio-labelled RTX of Example 1 as the active ingredient is combined with 187 mg of microcrystalline cellulose as a carrier, 9 mg of stearic acid and 2 mg of colloidal silica. These materials are pressed to form a tablet.

EXAMPLE 9

A tablet is formulated and prepared as in Example 8. The tablet is orally administered to a patient and 4–5 tablets represent a typical daily dosage.

All publications including U.S. patents and literature references as well as all copending patent applications referred to in this application are herein incorporated by reference.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What we claim is:

1. An isolated compound consisting essentially of radiolabelled resiniferatoxin.

2. The isolated labelled resiniferatoxin of claim 1, wherein the label is selected from the group consisting of a tritium label and an iodine label.

3. The compound selected from the group consisting of tritium labelled resiniferatoxin, I-131 labelled resiniferatoxin and I-125 labelled resiniferatoxin.

4. Isolated labelled resiniferatoxin.

5. The compound of claim 4 wherein said resiniferatoxin or congeners thereof having the formula:

where $R_3$ is OH, X is 0 or 1, $R_1$, $R_2$, $R_4$ and $R_5$ each are: H, OH with n=0 to 10 are fluorescently labeled.

6. The compound of claim 5, wherein the fluorescent labels are selected from the group consisting of fluorescein, rhodamine, eosin, erythrosin, pyrene, anthracene, acridine, dimethylaminophytyl and 7-nitrobenzo-2-oxa-1,3-diazole (NBD).

7. Tritium or iodine radiolabelled resiniferatoxin.

8. A labelled compound having the formula:

[structure of resiniferatoxin congener with CH₂OCR group at position 20]

where $$R = (CH_2)_x \underset{R_5}{\overset{R_1}{\bigcirc}} \begin{matrix} R_2 \\ R_3 \\ R_4 \end{matrix}$$

$R_3$ is OH, X is 0 or 1, $R_1$, $R_2$, $R_4$ and $R_5$ each are: H, OH, $$\overset{O}{\underset{}{\overset{\|}{OC}}}(CH_2)_nH, \ O(CH_2)_nH$$

with n = 0 to 10.

wherein at least one of $R_1$, $R_2$, $R_4$, or $R_5$ is labelled with $^3H$, $^{125}I$ or $^{131}I$.

9. Isolated radiolabelled congeners of resiniferatoxin having the formula:

[structure of resiniferatoxin congener]

where $$R = (CH_2)_x \underset{R_5}{\overset{R_1}{\bigcirc}} \begin{matrix} R_2 \\ R_3 \\ R_4 \end{matrix}$$

$R_3$ is OH, X is 0 or 1, $R_1$, $R_2$, $R_4$ and $R_5$ each are: H, OH, $$\overset{O}{\overset{\|}{OC}}(CH_2)_nH, \text{ or } O(CH_2)_nH$$

with n = 0 to 10

10. Radiolabelled congeners of resiniferatoxin having the formula:

[structure of resiniferatoxin congener]

where

$$R = (CH_2)_x \underset{R_5}{\overset{R_1}{\bigcirc}} \begin{matrix} R_2 \\ R_3 \\ R_4 \end{matrix}$$

$R_3$ is OH, X is 0 or 1, $R_1$, $R_2$, $R_4$ and $R_5$ each are: H, OH,

$$\overset{O}{\overset{\|}{OC}}(CH_2)_nH, \text{ or } O(CH_2)_nH$$

with n = 0 to 10, wherein the label is selected from the group consisting of a tritium label and an iodine label.

11. The compound having the formula:

where $R_3$ is OH, X is 0 or 1, $R_1$, $R_2$, $R_4$ and $R_5$ each are: H, OH, with n=0 to 10, and at least one $R_1$, $R_2$, $R_4$ or $R_5$ is labelled with $^3H$, $^{125}I$ or $^{131}I$.

12. The compound of claim 11, wherein said congener has the formula:

wherein R' is a fluorescent label and n is 0 to 10.

13. Isolated radiolabelled tinyatoxin.

14. The compound having the formula

15. The compound having the formula where X is 1—3.

16. The compound of claim 15, wherein X is 1 or 2.

17. The compound having the formula

18. The compound having the formula

19. The compound having the formula

20. The compound having the formula

21. The compound having the formula where X is 1-3.

22. The compound of claim 21, wherein X is 1 or 2.

23. The compound having the formula

24. The compound having the formula

25. The compound having the formula

26. The compound having the formula

-continued

27. A composition comprising an effective amount of the compound of claim 1 for use in receptor binding and a suitable carrier.

28. A composition comprising an effective amount of the compound of claim 3 for use in receptor binding and a suitable carrier.

29. A composition comprising an effective amount of the compound of claim 5 for use in receptor binding and a suitable carrier.

30. A method for detecting a capsaicin receptor in a subject, which comprises administering to a subject the labelled compound of claim 1, and measuring the amount of said labelled compound in said subject.

* * * * *